(12) United States Patent
Chian et al.

(10) Patent No.: US 9,939,384 B2
(45) Date of Patent: *Apr. 10, 2018

(54) LOW-POWERED SYSTEM FOR DRIVING A FUEL CONTROL MECHANISM

(71) Applicant: Honeywell International Inc., Morris Plains, NJ (US)

(72) Inventors: Brent Chian, Plymouth, MN (US); David Kucera, Bilovice nad Svitavou (CZ); Trevor C. Haag, Fridley, MN (US); Timothy J. Nordberg, Edina, MN (US); Adam Foley, Blaine, MN (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,765

(22) Filed: Sep. 18, 2017

(65) Prior Publication Data

US 2018/0003643 A1   Jan. 4, 2018

Related U.S. Application Data

(63) Continuation of application No. 15/676,691, filed on Aug. 14, 2017, which is a continuation of application
(Continued)

(51) Int. Cl.
*H01H 47/00* (2006.01)
*G01N 21/78* (2006.01)
(Continued)

(52) U.S. Cl.
CPC ............. *G01N 21/78* (2013.01); *F23N 1/002* (2013.01); *F23N 5/242* (2013.01);
(Continued)

(58) Field of Classification Search
CPC ..................................................... G01N 21/78
See application file for complete search history.

(56) References Cited

U.S. PATENT DOCUMENTS

| 3,489,350 A | 1/1970 | Caparone |
| 3,715,669 A | 2/1973 | LaForest |
(Continued)

FOREIGN PATENT DOCUMENTS

| DE | 3020228 A1 | 12/1981 |
| DE | 10203765 A1 | 8/2003 |
(Continued)

*Primary Examiner* — Stephen W Jackson
(74) *Attorney, Agent, or Firm* — Seager, Tufte & Wickhem, LLP

(57) ABSTRACT

A low powered system for providing sufficient current to a fuel control mechanism drive. The system may have a fuel control mechanism pick circuit that has an energy storage mechanism for providing a large amount of current for a short time to the fuel control mechanism drive. A safety switch may be enabled with a special signal to let current flow to the fuel control mechanism drive to operate a corresponding fuel control mechanism for controlling fuel to a pilot light or heating element. The pilot light or heating element may provide heat to a thermoelectric source that generates electrical power from the heat. The electrical power may go to a single DC-to-DC converter and voltage clamp for providing a voltage source to a microcontroller and other circuits of the system. The pick circuit may prevent a harmful reverse flow of current from the storage mechanism to the thermoelectric source.

30 Claims, 17 Drawing Sheets

Related U.S. Application Data

No. 14/042,269, filed on Sep. 30, 2013, now Pat. No. 9,752,990.

(51) Int. Cl.
*F23N 5/24* (2006.01)
*F23N 1/00* (2006.01)

(52) U.S. Cl.
CPC ...... *F23N 2023/08* (2013.01); *F23N 2031/02* (2013.01); *F23N 2031/10* (2013.01); *F23N 2031/18* (2013.01); *F23N 2031/22* (2013.01)

(56) References Cited

U.S. PATENT DOCUMENTS

| | | | |
|---|---|---|---|
| 3,847,350 A | 11/1974 | Thompson | |
| 4,118,750 A | 10/1978 | Auer, Jr. et al. | |
| 4,131,413 A | 12/1978 | Ryno | |
| 4,197,082 A | 4/1980 | Matthews | |
| 4,260,362 A | 4/1981 | Matthews | |
| RE30,936 E | 5/1982 | Kmetz et al. | |
| 4,459,099 A | 7/1984 | Grunden et al. | |
| 4,696,639 A * | 9/1987 | Bohan, Jr. | F23N 5/102 137/66 |
| 4,700,888 A | 10/1987 | Samulak | |
| 4,734,658 A | 3/1988 | Bohan, Jr. | |
| 4,770,629 A | 9/1988 | Bohan, Jr. | |
| 4,834,284 A | 5/1989 | Vandermeyden | |
| 4,865,538 A | 9/1989 | Scheele et al. | |
| 4,886,114 A | 12/1989 | Perkins et al. | |
| 4,920,473 A | 4/1990 | Frankenberg et al. | |
| 4,978,058 A | 12/1990 | Duncan et al. | |
| 4,984,981 A | 1/1991 | Pottebaum | |
| 4,993,401 A | 2/1991 | Diekmann et al. | |
| 4,995,415 A | 2/1991 | Weber | |
| 5,026,270 A | 6/1991 | Adams et al. | |
| 5,039,006 A | 8/1991 | Habegger | |
| 5,057,734 A | 10/1991 | Tsuzuki et al. | |
| 5,074,780 A | 12/1991 | Erdman | |
| 5,085,574 A | 2/1992 | Wilson | |
| 5,181,846 A | 1/1993 | Chang | |
| 5,203,688 A | 4/1993 | Dietiker | |
| 5,307,990 A | 5/1994 | Adams et al. | |
| 5,403,182 A | 4/1995 | Toth et al. | |
| 5,427,086 A | 6/1995 | Brownell | |
| 5,431,182 A | 7/1995 | Brown | |
| 5,442,157 A | 8/1995 | Jackson | |
| 5,494,215 A | 2/1996 | Drummond et al. | |
| 5,518,396 A | 5/1996 | Muzzolini et al. | |
| 5,539,672 A | 7/1996 | Mullin et al. | |
| 5,588,637 A | 12/1996 | Carsten et al. | |
| 5,622,200 A | 4/1997 | Schulze | |
| 5,660,328 A | 8/1997 | Momber | |
| 5,720,608 A | 2/1998 | Aoki et al. | |
| 5,768,116 A | 6/1998 | Kompelien | |
| 5,769,622 A | 6/1998 | Aoki et al. | |
| 5,773,969 A | 6/1998 | Nakayama et al. | |
| 5,797,358 A | 8/1998 | Brandt et al. | |
| 5,815,365 A | 9/1998 | Stege | |
| 5,844,786 A | 12/1998 | Yoshida et al. | |
| 5,865,538 A | 2/1999 | Walker et al. | |
| 5,889,645 A | 3/1999 | Kadah et al. | |
| 5,917,691 A | 6/1999 | Kadah | |
| 5,931,655 A | 8/1999 | Maher, Jr. | |
| 5,975,884 A | 11/1999 | Dugger | |
| 6,050,281 A | 4/2000 | Adams et al. | |
| 6,059,195 A | 5/2000 | Adams et al. | |
| 6,069,804 A | 5/2000 | Ingman et al. | |
| 6,097,585 A | 8/2000 | Heinzelmann et al. | |
| 6,150,601 A | 11/2000 | Schnatzmeyer et al. | |
| 6,158,715 A | 12/2000 | Kirschbaum | |
| 6,192,687 B1 | 2/2001 | Pinkerton et al. | |
| 6,257,264 B1 | 7/2001 | Sturman et al. | |
| 6,261,087 B1 | 7/2001 | Bird et al. | |
| 6,280,180 B1 | 8/2001 | Fredin-Garcia-Jurado et al. | |
| 6,293,471 B1 | 9/2001 | Stettin et al. | |
| 6,335,572 B1 | 1/2002 | Uno et al. | |
| 6,346,789 B1 | 2/2002 | Bird et al. | |
| 6,382,961 B2 | 5/2002 | Clifford et al. | |
| 6,407,902 B1 | 6/2002 | Patty et al. | |
| 6,410,842 B1 | 6/2002 | McAlonan | |
| 6,419,478 B1 | 7/2002 | Kemp | |
| 6,428,308 B1 | 8/2002 | Bird et al. | |
| 6,478,573 B1 | 11/2002 | Chian | |
| 6,519,508 B1 | 2/2003 | Saito | |
| 6,545,852 B1 | 4/2003 | Arnold | |
| 6,598,405 B2 | 7/2003 | Bell | |
| 6,631,067 B2 | 10/2003 | Newton et al. | |
| 6,633,726 B2 | 10/2003 | Bradenbaugh | |
| 6,667,594 B2 | 12/2003 | Chian | |
| 6,685,159 B1 | 2/2004 | Schnell | |
| 6,701,874 B1 | 3/2004 | Schultz et al. | |
| 6,708,083 B2 | 3/2004 | Orthlieb et al. | |
| 6,722,876 B2 | 4/2004 | Abraham et al. | |
| 6,862,165 B2 | 3/2005 | Chian et al. | |
| 6,862,455 B1 | 3/2005 | Costa et al. | |
| 6,881,055 B2 | 4/2005 | Bird | |
| 6,895,997 B2 | 5/2005 | Qu et al. | |
| 6,920,377 B2 | 7/2005 | Chian | |
| 6,920,843 B1 | 7/2005 | Wilson | |
| 6,955,301 B2 | 10/2005 | Munsterhuis et al. | |
| 6,959,876 B2 | 11/2005 | Chian et al. | |
| 7,073,524 B2 | 7/2006 | Chian | |
| 7,076,373 B1 | 7/2006 | Munsterhuis et al. | |
| 7,167,813 B2 | 1/2007 | Chian et al. | |
| 7,170,762 B2 | 1/2007 | Chian et al. | |
| 7,208,928 B2 | 4/2007 | Nebrigic et al. | |
| 7,252,502 B2 | 8/2007 | Munsterhuis | |
| 7,314,370 B2 | 1/2008 | Chian et al. | |
| 7,317,265 B2 | 1/2008 | Chian et al. | |
| 7,435,081 B2 | 10/2008 | Munsterhuis | |
| 7,586,213 B2 | 9/2009 | Vegter | |
| 7,712,677 B1 | 5/2010 | Munsterhuis et al. | |
| 7,798,107 B2 | 9/2010 | Chian et al. | |
| 7,804,047 B2 | 9/2010 | Zak et al. | |
| 7,804,199 B2 | 9/2010 | Vegter | |
| 7,841,440 B2 | 11/2010 | Liu | |
| 8,165,726 B2 | 4/2012 | Nordberg et al. | |
| 8,177,544 B2 | 5/2012 | Anderson | |
| 8,322,312 B2 | 12/2012 | Strand | |
| 8,636,502 B2 | 1/2014 | Anderson | |
| 8,875,664 B2 | 11/2014 | Strand | |
| 9,388,984 B2 | 7/2016 | Anderson | |
| 9,410,719 B2 | 8/2016 | Furmanek et al. | |
| 9,568,196 B2 | 2/2017 | Furmanek et al. | |
| 9,574,793 B2 | 2/2017 | Furmanek et al. | |
| 9,599,369 B2 | 3/2017 | Furmanek et al. | |
| 9,752,990 B2 * | 9/2017 | Chian | G01N 21/78 |
| 2001/0031138 A1 | 10/2001 | Troost, IV | |
| 2002/0132202 A1 | 9/2002 | Clifford | |
| 2003/0091091 A1 | 5/2003 | Patterson et al. | |
| 2005/0130086 A1 | 6/2005 | MacNutt et al. | |
| 2006/0141409 A1 | 6/2006 | Chian et al. | |
| 2015/0090310 A1 | 4/2015 | Chian et al. | |

FOREIGN PATENT DOCUMENTS

| | | |
|---|---|---|
| DE | 102004016764 B3 | 9/2005 |
| EP | 0322899 A2 | 12/1988 |
| EP | 0717332 A1 | 6/1996 |
| EP | 1020688 A2 | 7/2000 |
| JP | 63106002 A | 5/1988 |
| WO | 0138792 A1 | 5/2001 |

* cited by examiner

LOW-POWERED SYSTEM FOR DRIVING A FUEL CONTROL MECHANISM

This is a continuation application of co-pending U.S. patent application Ser. No. 15/676,691, filed Aug. 14, 2017, and entitled "A LOW-POWERED SYSTEM FOR DRIVING A FUEL CONTROL MECHANISM", which is a continuation application of U.S. patent application Ser. No. 14/042,269, filed Sep. 30, 2013, and entitled "A LOW-POWERED SYSTEM FOR DRIVING A FUEL CONTROL MECHANISM" now U.S. Pat. No. 9,752,990, issued Sep. 5, 2017, both of which are incorporated herein by reference.

BACKGROUND

The present disclosure pertains to combustion control devices and particularly to low power combustion control devices. More particularly, the disclosure pertains to safe low power combustion control devices.

SUMMARY

The disclosure reveals a low-powered system. The system may have a fuel control mechanism pick circuit which has an energy storage mechanism for providing a large amount of current for a short time to a fuel control mechanism drive. A safety switch may control whether current can flow to the fuel control mechanism drive to operate a corresponding fuel control mechanism for controlling fuel to a pilot light or a heating element. The pilot light or heating element may provide heat to a thermoelectric source that generates electrical power from the heat. The power may go to a DC-to-DC converter and voltage clamp for providing a voltage source to a microcontroller and other circuits of the system. The safety switch may receive a special signal to enable a flow of current from the storage mechanism to the fuel control mechanism drive. The pick circuit may prevent a reverse flow of current from the storage mechanism to the thermoelectric source that could harm the thermoelectric source. The microcontroller may provide an available low magnitude flow of current to charge up the storage mechanism; however, such current is not necessarily sufficient for the fuel control mechanism drive. The microcontroller may also provide the special signal to the safety switch to enable a sufficient flow of current from the storage mechanism to the fuel control mechanism drive. The fuel control mechanism may control fuel to the pilot light and/or heating element of a water heater, stove, furnace, and other appliances.

DESCRIPTION

Figure 1:
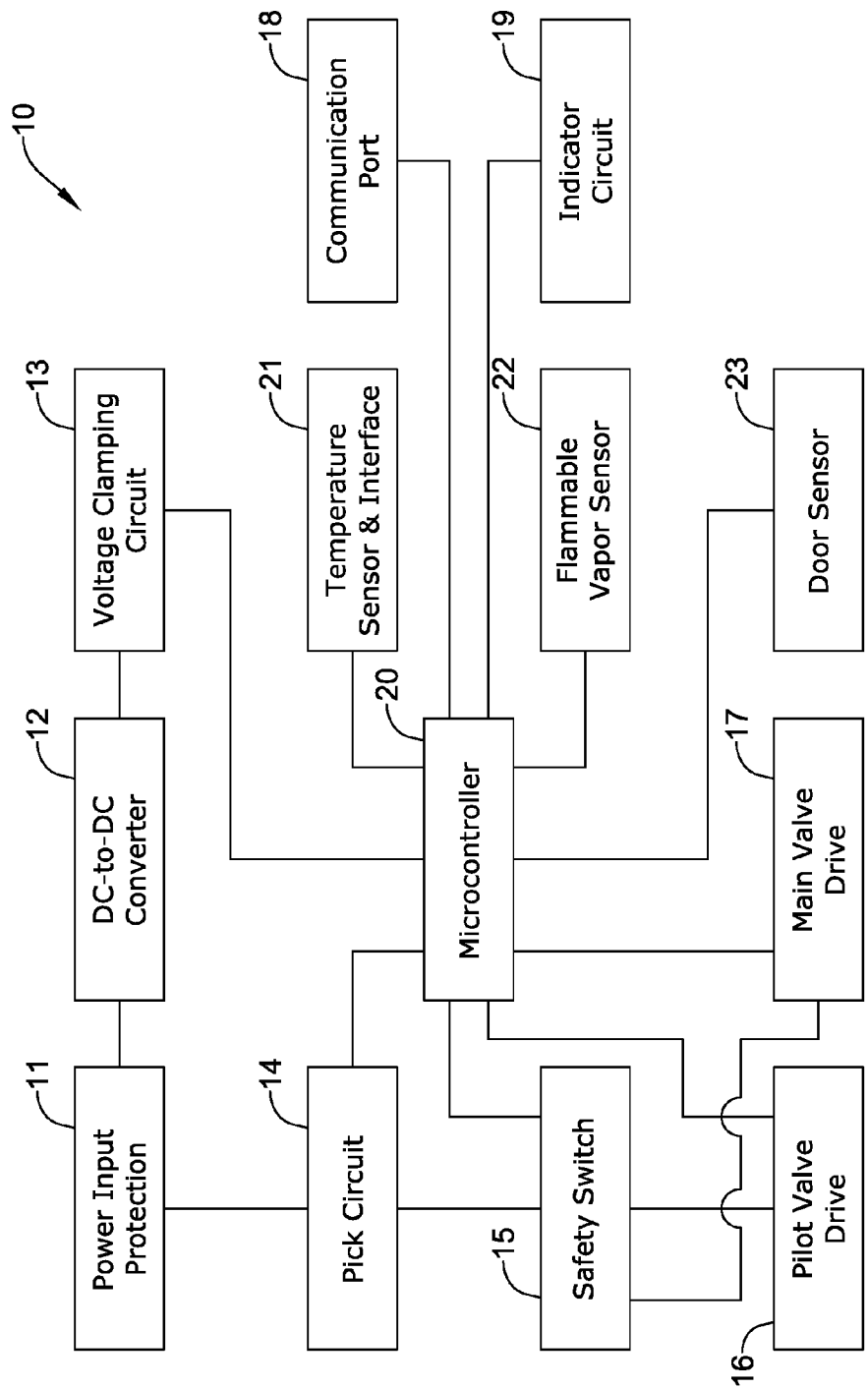
FIG. 1 is a diagram of an example illustrative fuel control system.

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

In a flame powered combustion system, a microcontroller may actively manage the flame generated power to run the valves and the electronics. Active management itself may take some power, and the system cost may be higher with an actively controlled DC-to-DC converter. Thus, an actively controlled DC-to-DC converter may not necessarily be used. The microcontroller may be kept in sleep mode as much as possible to reduce power consumption. A free-running DC-to-DC converter may be improved for high efficiency, and be structured to take limited power from a source.

The transformer used in the free-running DC-to-DC converter may be designed so that at the critical input voltage level (closed-circuit input voltage of about 155 mV). The DC-to-DC converter may take just enough power to keep the microcontroller running while the pilot and main valves can be held in. This approach may be referred to "built-in optimized power sharing".

The active power management procedure may be minimal. Since the microcontroller does not necessarily need to generate a pulse wave modulated (PWM) signal, the microcontroller may stay in a deep sleep mode instead of idle mode whenever not in active mode, thus consuming less power. A valve picking circuit and safety switch may be designed to use a small amount of energy for valve picking. Flame powered combustion controls may run with a power source generated from pilot flame. The output power from the power source may be very limited.

In a flame powered water heater control, a valve picking circuit may be used to store energy for valve picking, and a safety switch may be used to safe guard against a possible microcontroller malfunction.

A valve-picking circuit may be designed to improve the energy efficiency during valve picking time. A switch may be added between the power source and the safety switch, so that the valve picking circuit can apply full voltage stored on a capacitor to the valve during valve picking time. With the added switch, the efficiency may be about doubled in the valve picking process.

An N-channel MOSFET may be used for the safety switch. A PNP BJT may be added in the gate drive for the MOSFET. The drive signal might only be produced when the controller is driving an I/O pin actively.

A fail-safe flame powered combustion control valve may be noted. Combustion controls should be designed to be fail-safe, which may often require additional components or software tests to ensure that a product is fully functional during startup and operation.

An electronic pilot valve control may employ redundant transistors to operate the valve coils, and require a specific dynamic drive of the circuit (from the microcontroller) to hold the valve or valves open (i.e., flowing gas).

The present approach may add additional protection for the microcontroller pin toggling failure modes. The approach may do so in a low-cost manner requiring very few parts.

The present circuit may first use two I/O pins to charge a capacitor. Once the capacitor is properly charged, then the charge on the capacitor may keep a bipolar junction transistor forward biased to turn on a MOSFET that serves as a safety switch (i.e., redundant valve drive). If the microcontroller fails such that virtually all of its I/O pins are toggling in the same manner, the capacitor is not necessarily charged and the safety switch would remain in the OFF state.

Figure 4:
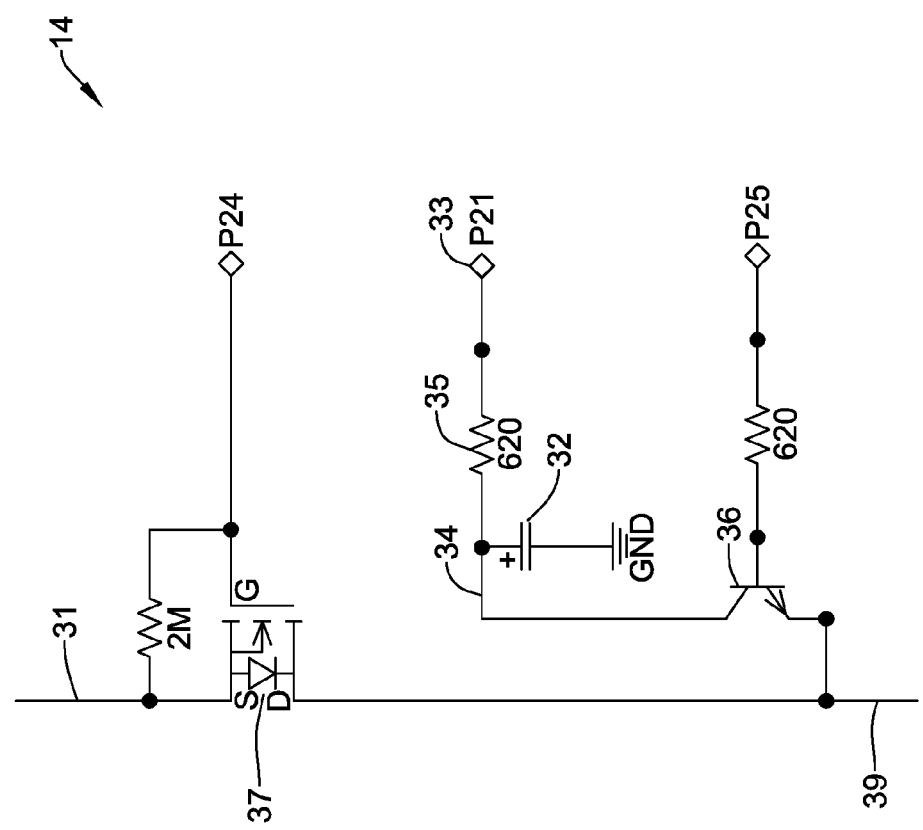
FIG. 4 is a diagram of a pick circuit.

FIG. 4 is a diagram of a pick circuit 14. A transistor 37 may be noted. During valve pick time, transistor 37 may be off, preventing current flow back to flame power input 71. Capacitor 32 may be charged to 2.2 volts or higher before picking a valve. 3.4 volts may be needed in other designs. When picking a valve, transistor 36, transistor 38 and transistor 52 or 53 may be turned on. Current may flow from capacitor 32 to the respective valve (connected at terminal 73 and/or terminal 74). A voltage applied to the valve is not necessarily restricted to a certain level.

To turn on transistor 38, microcontroller 20 should toggle at pin 41 at a frequency higher than a few hundred Hz with a high duty cycle. This may produce a voltage signal to turn on transistor 43 for most of the time. Parasitic gate capacitance of transistor 38 may keep transistor 38 on during a short low time at pin 41.

Safety switch 15 may be safe as high input voltage can not necessarily turn the safety switch on. Safety switch 15 may be safe as it is in a path of picking current. The present circuit may have low cost and a low component count. For instance, there may be no need for a P-channel MOSFET on a printed circuit board of switch 15, no need of an interlock switch with DC-to-DC converter 12, no more than one stage of a charge pump, and no more dedicated turn-off circuit.

There may be good power management during pick time as the DC-to-DC converter 12 may be active. The present circuit may be turned on instantly. Since transistor 37 may be incorporated, safety switch 15 does not necessarily need be turned off quickly. When toggling at pin 41 stops, safety switch 51 may be off in a few hundreds of a micro-second.

Since safety switch 15 may be turned on instantly, and the transition from on-state to off-state may be quickly detected, the health of safety switch 15 may be checked almost any time (i.e., during start up, and run or idle time) and as frequently as necessary, thus improving safety features of control.

A safety switch transistor 38 may be an N-channel MOSFET. If pin 41 is toggled with a high-duty waveform and pin 42 has an output high state, capacitor 44 may be charged and then transistor 43 may be turned on. When transistor 43 is in an ON state, transistor 38 may also be turned on. However, if pins 41 and 42 are toggled at the same frequency and phase, then capacitor 44 will not necessarily be charged, and transistor 43 and safety switch transistor 38 will remain in an OFF state.

FIG. 1 is a diagram of an example illustrative control system 10. Power may be available to a power input protection module 11. An output from module 11 may go to a DC-to-DC converter 12, and an output from converter 12 may go to a voltage clamping circuit 13. Circuit 13 may provide a component supply voltage (Vcc) to a microcontroller 20. The voltage may also be provided to other electronic components of system 10.

Another output from module 11 may be provided to a pick circuit 14. Circuit 14 may be connected to a safety switch 15 and microcontroller 20.

Figure 8:
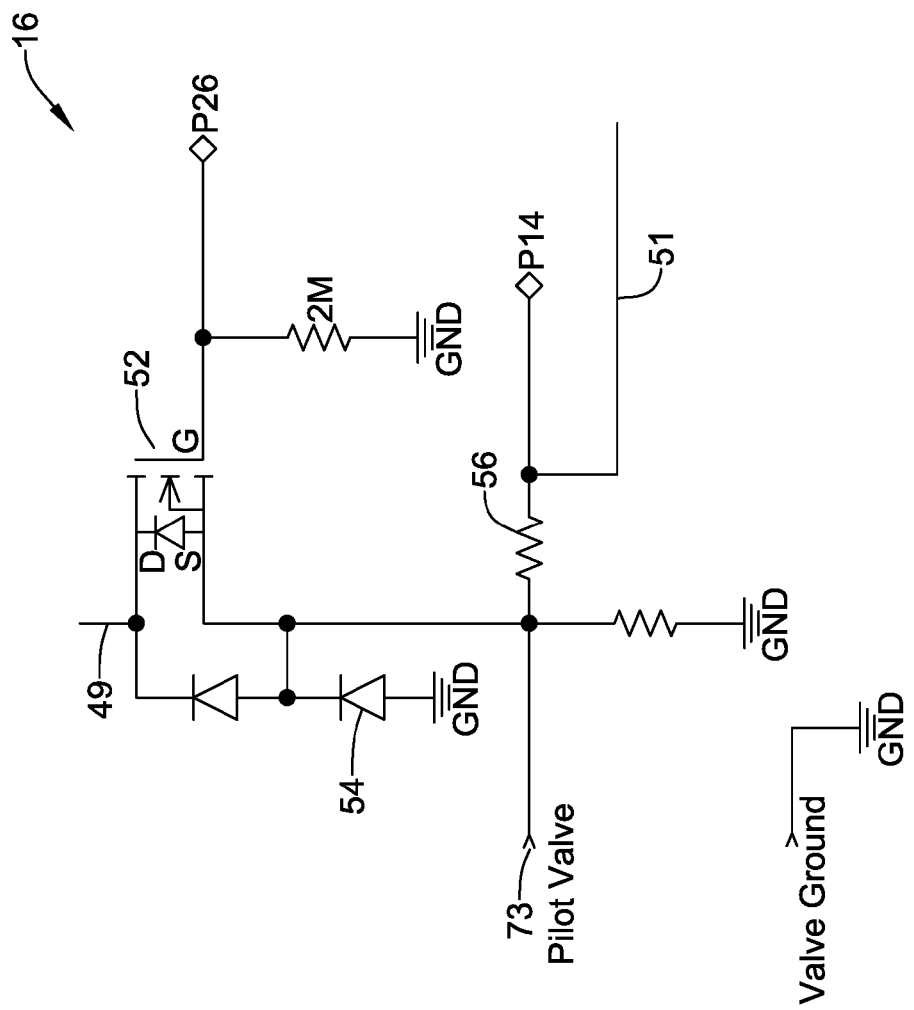
FIG. 8 is a diagram of a pilot valve drive circuit.
Figure 9:
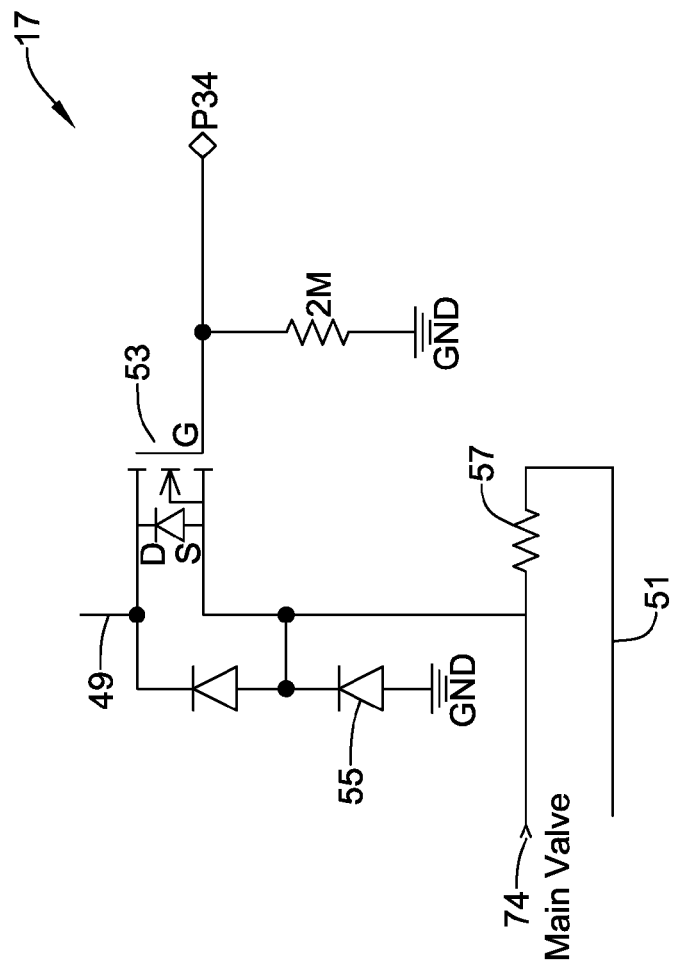
FIG. 9 is a diagram of a main valve drive circuit.

FIG. 8 is a diagram of a pilot valve drive circuit. FIG. 9 is a diagram of a main valve drive circuit. Safety switch 15 may be connected to pilot valve drive 16, main valve drive 17, and microcontroller 20. Pilot valve drive 16 and main valve drive 17 may also be connected to microcontroller 20.

A communication port 18 and an indicator circuit may be connected to microcontroller 20. A temperature sensor and knob interface 21, a flammable vapor sensor 22, and a door sensor 23 may be connected to microcontroller 20.

Figure 2:
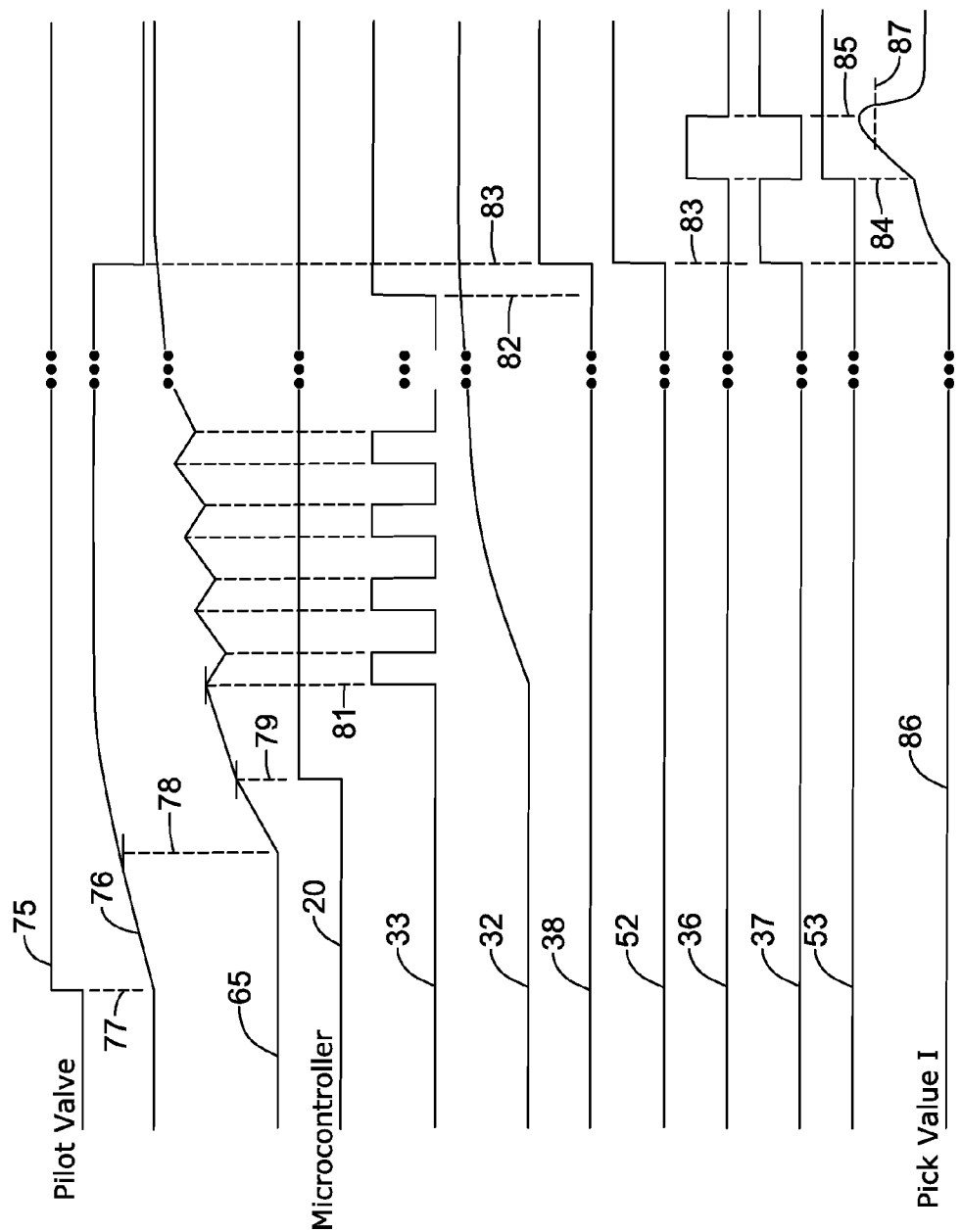
FIG. 2 is a diagram of traces of amplitudes of various components versus time for the control system.

FIG. 2 is a diagram of traces of amplitudes of signals of various components versus time for system 10. Trace 75 shows a pilot valve being opened by a user holding a knob down for a brief period of time and the pilot being lit at a time line 77. A voltage tp (Vtp) may begin at time line 77 to gain and achieve a certain amplitude as shown by a trace 76. When Vtp reaches about 150 millivolts at a time line 78, DC-to-DC converter 12 may start producing output current to charge capacitor 63. As a charge of a capacitor 63 reaches about 1.8 volts, at a time line 79, microcontroller 20 may enter an active mode. In one minute or so, the Vtp 76 trace may reach 700 millivolts. When the trace 65 of the charge on capacitor 63 reaches about 2.6 volts at a time line 81, then P21 of input 33 starts to change state between an output high and a high-impedance input. When it is in output high state, current flows from microcontroller to charge up capacitor 32. When it is in input state, capacitor 32 holds its charge. Trace 65 may have an up and flat or stepped affect superimposed on its increasing magnitude. Trace 33 may continue with the interchanging states of output high and high-impedance input to a time line 82 where a trace 32 of Vcap indicates that pick circuit 14 is ready to pick a valve. Trace 33 may remain at a high after time line 82.

At time line 83, transistor 38 may turn on and thus begin to pick a valve such as the pilot valve, where a transistor 52 turns on as indicated by trace 52 to energize the coil of the pilot valve to keep it open. A transistor 37 may turn on for about 40 milliseconds at time line 83 and then turn off for about 30 milliseconds at a time line 84. As transistor 37 turns off at time line 84, transistor 36 may turn on for about 30 milliseconds and then turn off at a time line 85 when transistor 37 turns back on. At timeline 83, a pick current may begin to build up. After transistor 36 is turned on at time line 84 the current will increase quickly and be sufficient, such as 35 milliamps, to pick a valve as indicated by trace 86. The current may increase to at least about 70 milliamps as indicated by amplitude 87 to guarantee a pilot valve pick. The magnitude of the pick current may be greater than 70 milliamps as indicated at time line 85. Shortly after time line 85, the valve picking may be complete and the current flowing to the valve coil may return to a lower, "hold" value.

Figure 3:
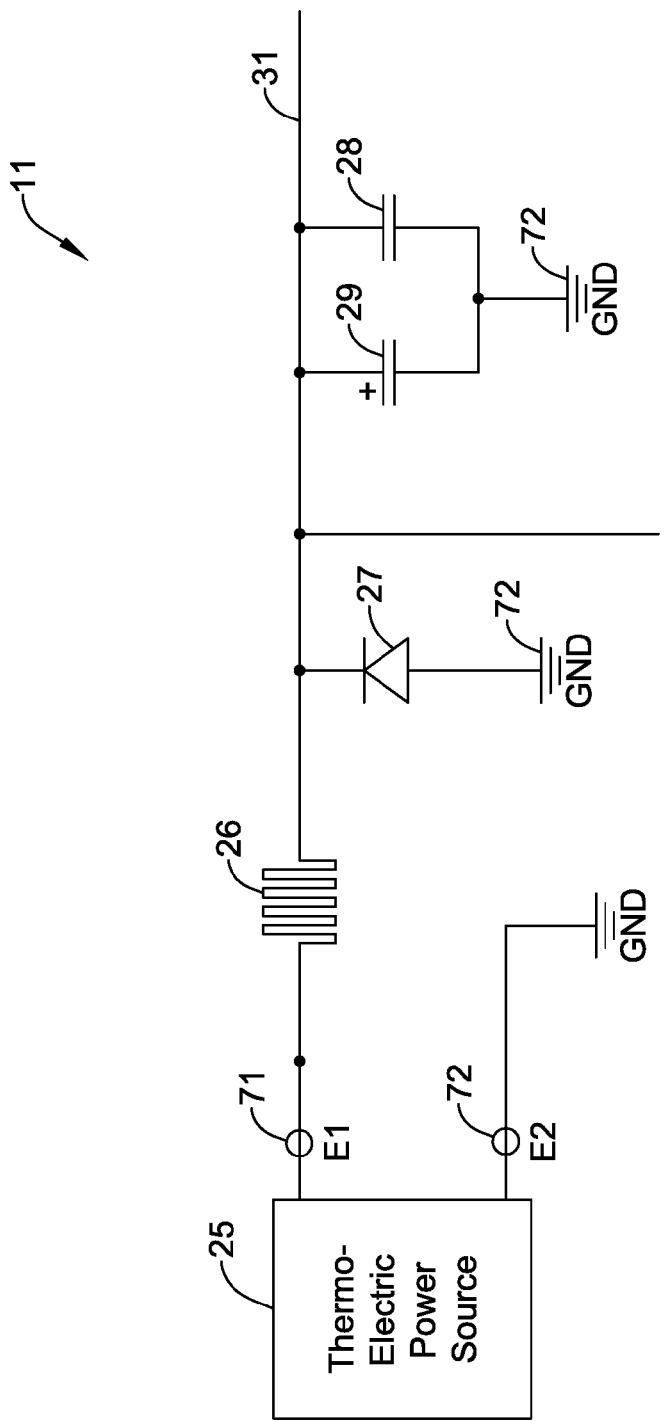
FIG. 3 is a diagram of a power input protection module.

FIG. 3 is a diagram of power input protection module 11. A supply current may come from a thermopile 25 at input 71 relative to a ground or reference voltage 72, and pass through a thin trace 26 on a printed circuit board. Thin trace 26 may act as a fuse in case of excessive input voltages to module 11, or to limit current in an event that a battery on DC power supply is connected. Diode 27 may offer protection in case an input voltage with a wrong polarity is connected to module 11. Diode 27 may prevent possible damage to circuits connected to module 11 by clamping the input voltage to a safe level. Capacitor 28 may prevent ESD from damaging MOSFETs. Capacitor 29 may be a tank capacitor that helps improve the efficiency of DC-to-DC converter 12.

FIG. 4 is a diagram of pick circuit 14. Line 31 of circuit 14 may be connected to line 31 of module 11. Pick circuit or valve picking circuit 14 may have a storage capacitor 32. An I/O pin 33 may be connected to microcontroller 20 to control charging of capacitor 32. Energy for picking a valve may be stored in capacitor 32 which is charged to a voltage 34 via a digital signal having current limited by a resistor 35. Charging capacitor 32 may be sequenced such that voltage 34 stays sufficiently high. After capacitor 32 charged above 2.2 volts, the energy stored on capacitor 32 may be enough for picking a valve. When a valve is picked, a transistor 36 may be turned on to allow current flow from capacitor 32 to a valve drive, and a transistor 37 may be turned off to prevent current flowing back to the thermopile input.

Figure 5:
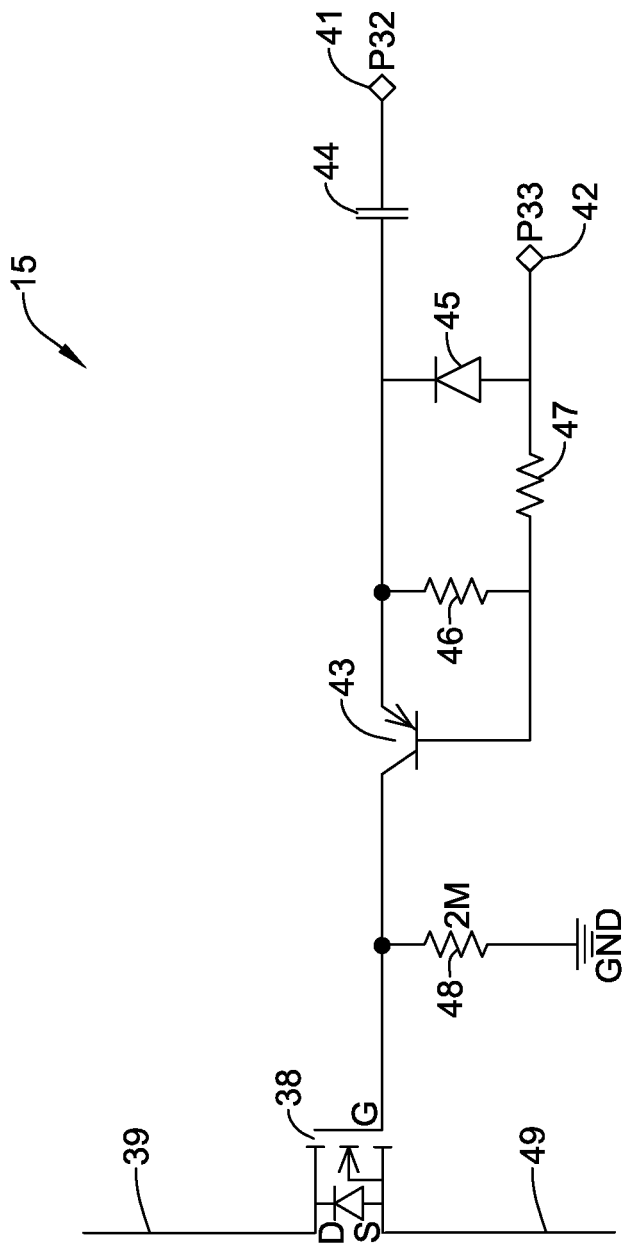
FIG. 5 is a diagram of a safety switch.

FIG. 5 is a diagram of a safety switch 15. A transistor 38 of safety switch 15 may be turned on to pick a valve. A picking sequence may differ for a pilot valve and a main valve. Transistor 38 may be an N-channel MOSFET and may act as the safety switch. Transistor 38 may be connected by a line 39 to pick circuit 14. Transistor 38 may be controlled by I/O pins 41 and 42 and an interface circuit having a transistor 43, a capacitor 44, a diode 45, a resistor 46 and a resistor 47. Microcontroller 20 may drive the interface circuit by toggling a digital output at pin 41 at a frequency and duty cycle such that pin 41 low time is short (such as shorter than 20 micro-second) and keeping pin 42 at a high state. The toggling signal may generate a high enough voltage to turn on transistor 43. When transistor 43 is on, then a positive voltage may be applied to the gate of transistor 38 and turn on transistor 38. If a signal on pin 41 stops toggling, or if the signal on pin 42 toggles together with the signal on pin 41 at the same frequency and phase, then transistor 43 may stay in an off state and transistor 38 is not driven. A resistor 48 may bleed the gate of transistor 38 to turn off transistor 38 if transistor 43 is not in an on state. Resistor 47 may limit the base current of transistor 43, and resistor 46 may prevent transistor 43 from being turned on by leakage.

The working conditions of safety switch 15 may be checked by the microcontroller 20 at least once per heating cycle of an associated heating system by reading a voltage across the valve coils. If safety switch 15 is found to be inoperable at any time, microcontroller 20 may take appropriate action to handle a fault condition.

Figure 6:
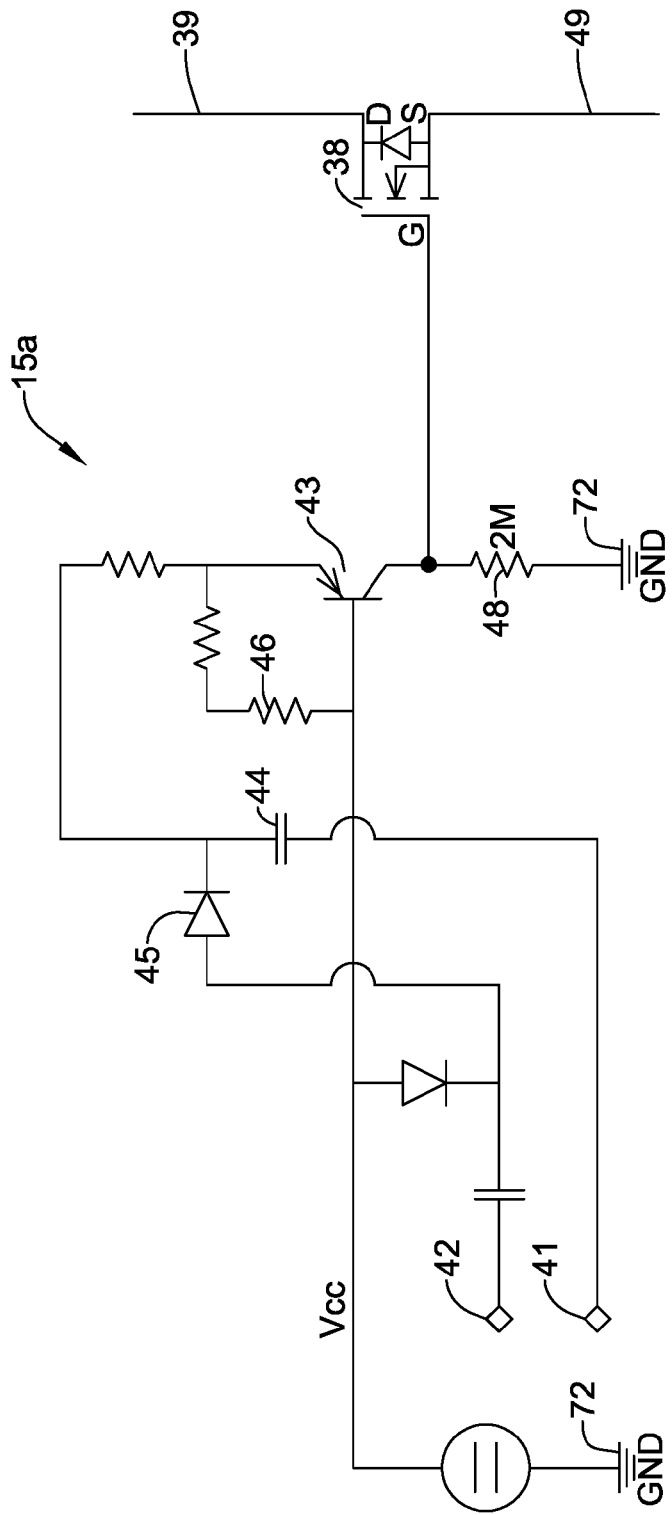
FIGS. 6 and 7 are diagrams of alternative safety switches.
Figure 7:
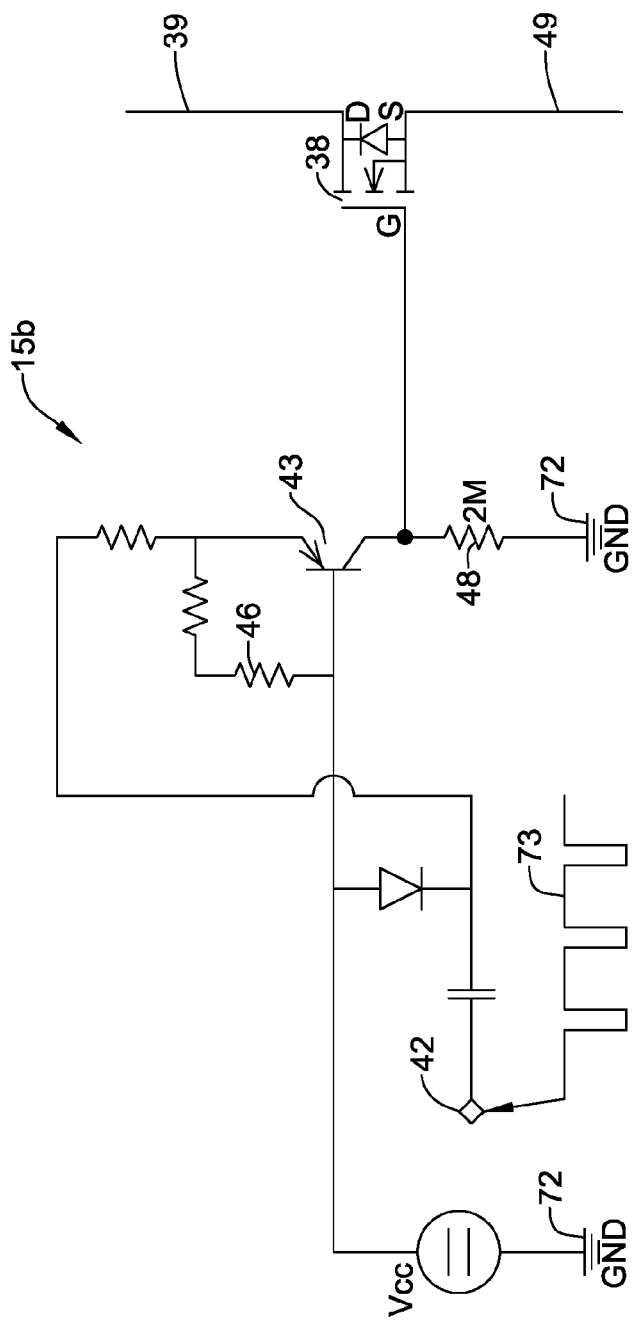

FIGS. 6 and 7 are diagrams of safety switches 15*a* and 15*b*, respectively, which may be used as alternative to safety switch 15 of FIG. 5. Unmarked components may be added with a variation in circuit detail relative to that in FIG. 5. In FIG. 7, a waveform of a duty cycle may toggle a pin input.

FIGS. 8 and 9 are diagrams of a pilot valve drive 16 and main valve drive 17. Working conditions of drives 16 and 17 may be checked by microcontroller 20 at least once per heating cycle by reading the voltage across each of the pilot and main valve coils. If a transistor is found to be inoperable at any time, microcontroller 20 may take the appropriate action to handle the fault condition.

Pilot drive 16 and main drive 17 may be in parallel with each other relative to a line 51, but in series with safety switch 15 on a line 49. The drivers, transistors 52 and 53, may be N-type FETs. To allow current to one of the valve coils, microcontroller 20 may set the gate of the appropriate transistor to high. Diodes 54 and 55 may provide a return current path to the valve coils when transistors 52 and 53, respectively, are turned off. Diodes 54 and 55 may also increase a level of ESD protection for the electronics. Resistors 56 and 57 of valve drives 16 and 17, respectively, may protect an ADC input (valve status sense) of microcontroller 20. Voltages on lines 73 and 74 may be combined to a single voltage for sensing by microcontroller 20.

Figure 10:
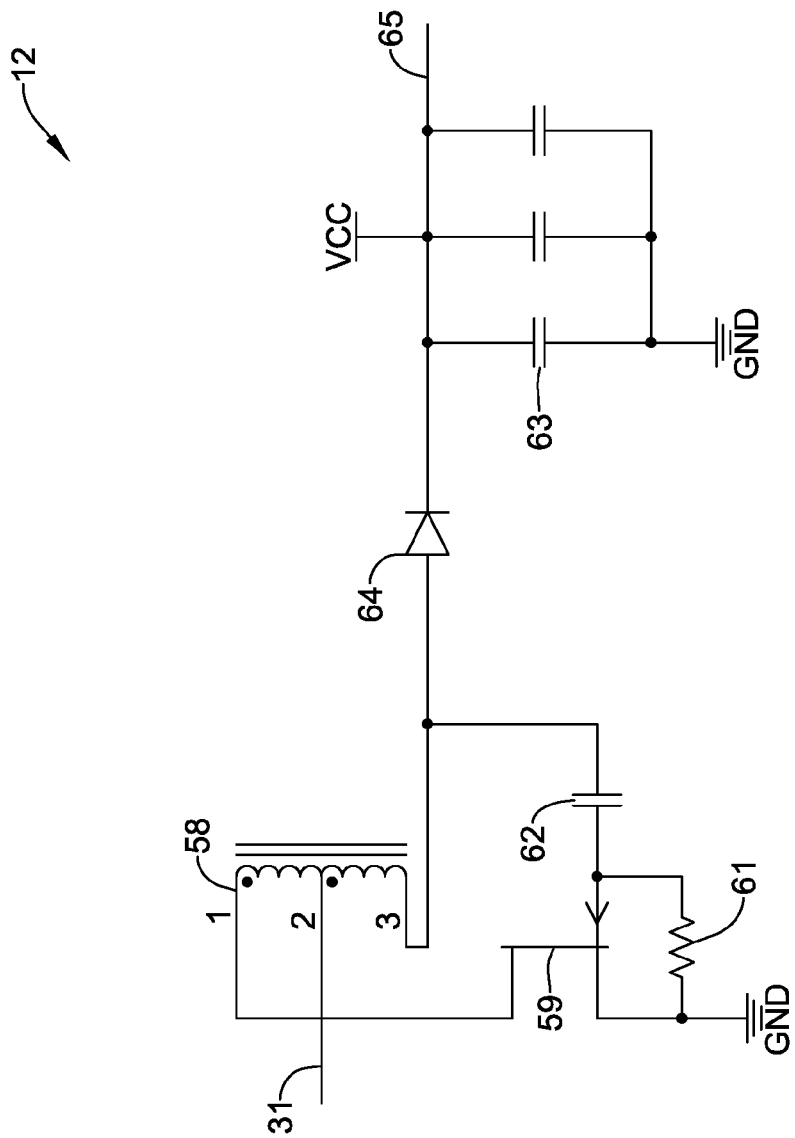
FIG. 10 is a diagram of a DC-to-DC converter circuit.

FIG. 10 is a diagram of DC-to-DC converter 12, which may be a low voltage step-up converter that starts to convert an input voltage to a higher voltage when the input voltage is about 150 millivolts or higher. Converter 12 may boost the voltage to above 2.0 volts in order to start microcontroller 20. Low-voltage DC-to-DC converter 12 may be a free-running oscillator having a transformer 58, a transistor 59, a resistor 61, and a capacitor 62. Capacitor 62 may provide a positive feedback to a gate of transistor 59 driving transistor 59 on and off with oscillations. Capacitor 62 may also provide a DC shift needed for optimum performance of the free-running oscillator. Toggling transistor 59 may cause an energy build-up in transformer 58 and cause the energy to be dumped from the secondary winding of transformer 58 to a storage capacitor 63 through a diode 64. Transistor 59 may be an N-channel depletion J-FET that conducts at zero Vgs. This characteristic may enable a start-up at very low input voltages. Resistor 61 may pull the gate of transistor 59 to zero voltage when control is not supplied, and thus get the circuit of converter 12 ready for a start-up.

Some example and illustrative specifications of converter 12 may be noted. Converter 12 may start a conversion with an input voltage equal to or greater than 150 millivolts. An output voltage should be greater than 2.0 volts after the input voltage is applied. With an input voltage of equal to or greater than 260 millivolts, converter 12 output voltage should be greater than 2.0 volts with microcontroller 20 functioning normally and the pilot valve open. With an input voltage equal to or greater than 330 millivolts, converter 12 output voltage should be higher than 2.0 volts with microcontroller 20 functioning normally and both the pilot and main valves open.

Figure 11:
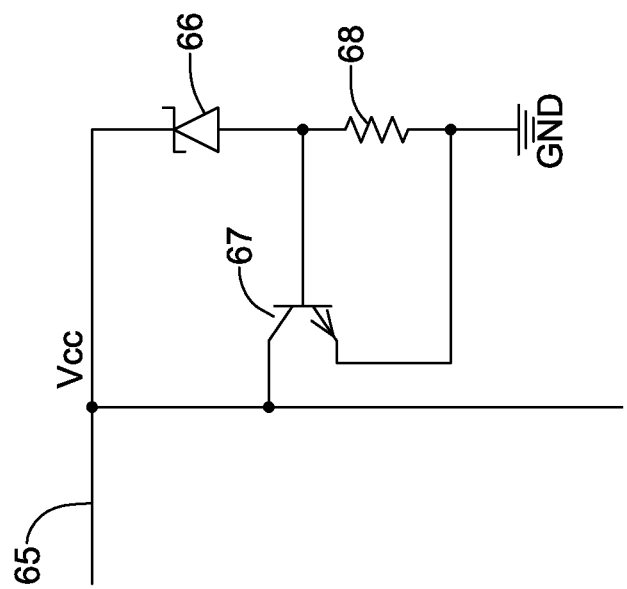
FIG. 11 is a diagram of a voltage clamping circuit.

FIG. 11 is a diagram of a voltage clamping circuit 13. Circuit 13 may have a line 65 connected to line 65 of converter 12. Line 65 may be regarded as a Vcc line. A zener diode 66, a transistor 67 and a resistor 68 may form the voltage clamping circuit. Circuit 13 may clamp Vcc to below 4.1 volts when a very strong thermopile (1.0 volt open circuit voltage) is connected to the board. The maximum voltage that microcontroller 20 can tolerate may be 4.1 volts.

Figure 12:
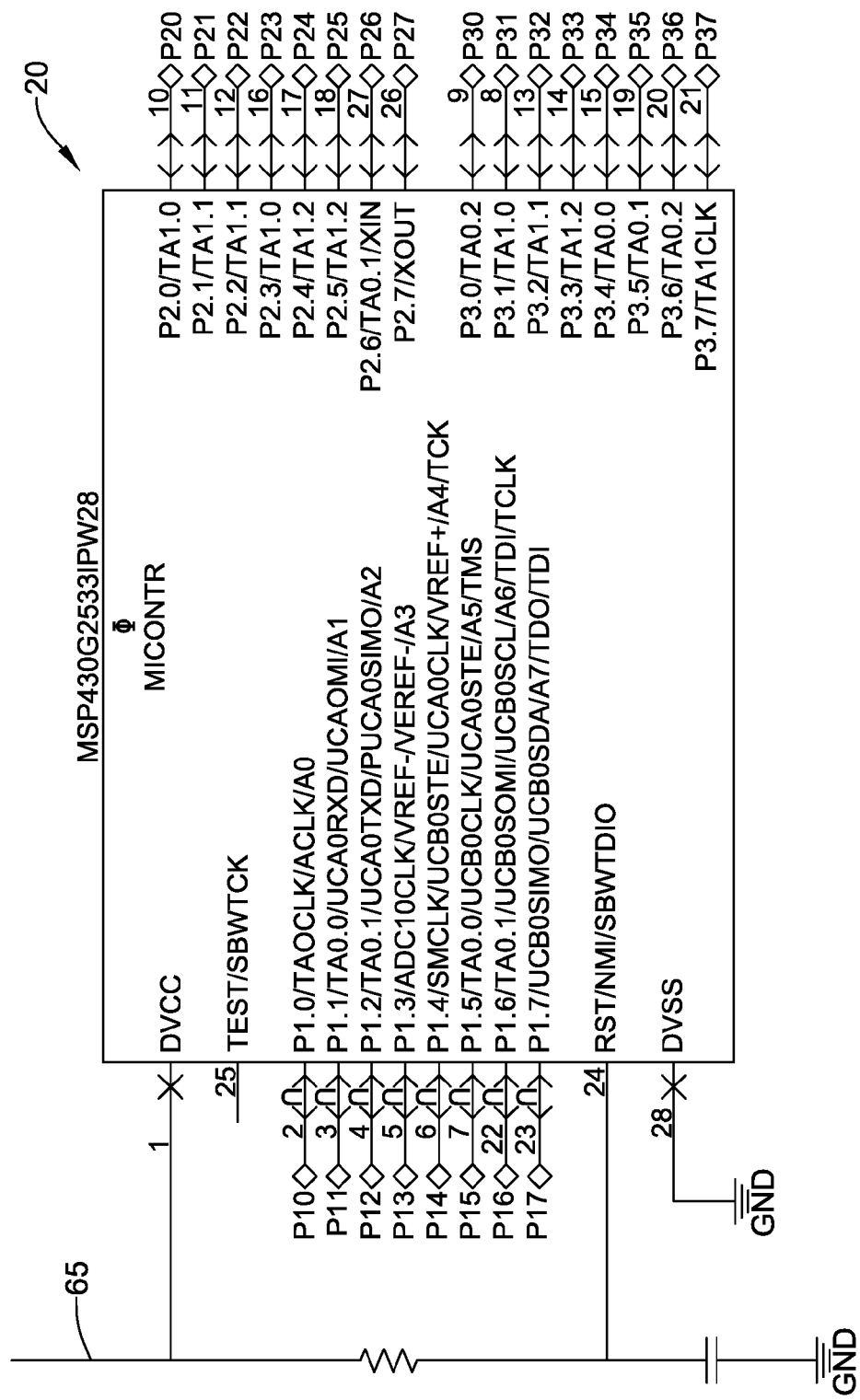
FIG. 12 is a diagram of a microcontroller.

FIG. 12 is a diagram of microcontroller 20. Terminal 1 of controller may be connected to a Vcc line 65 of voltage clamping circuit 13. Microcontroller 20 may an MSP430G2533 (TI). Pin numbers (i.e., I/O pins, e.g., P20) may be connected to lines of various components of system 10 as indicated by one or more lines labeled with a corresponding pin number (e.g., P20).

Figure 13:
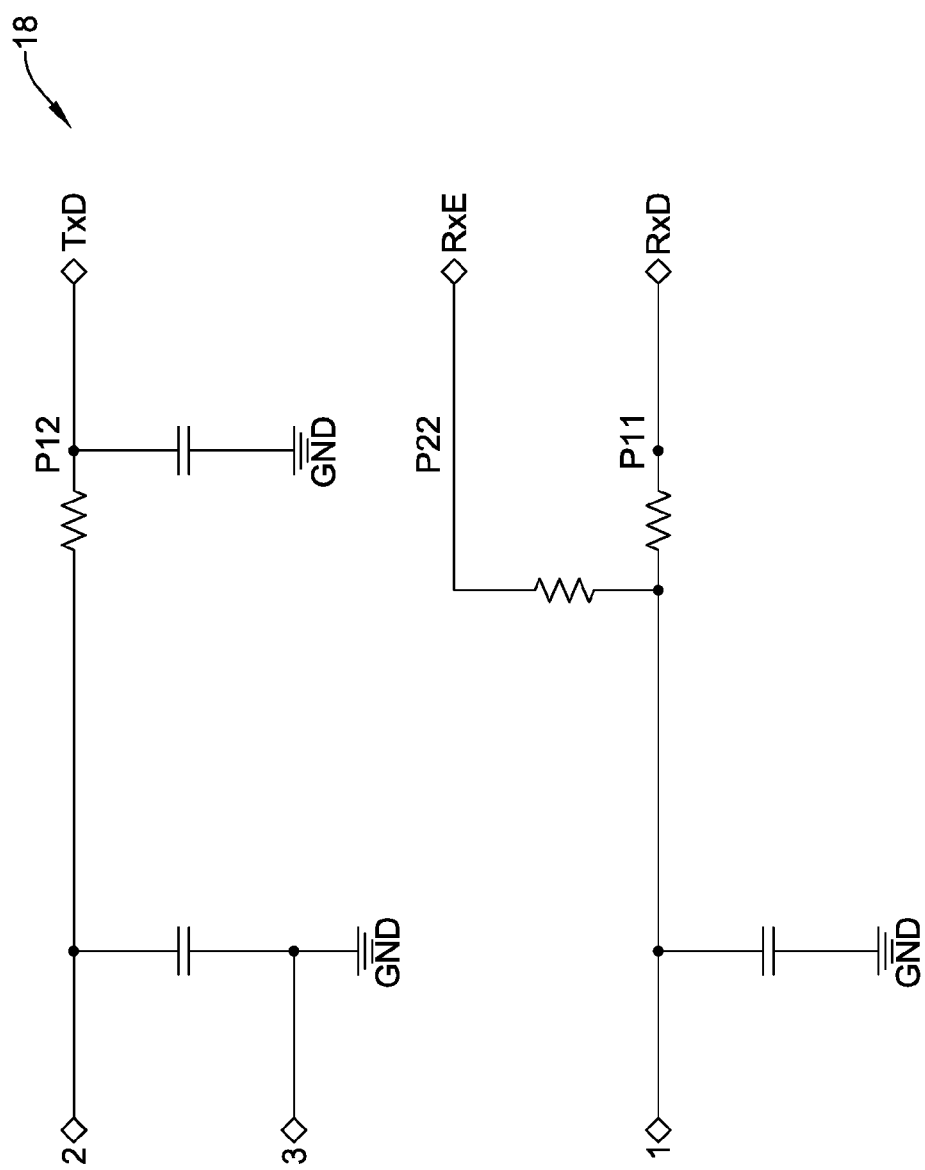
FIG. 13 is a diagram of circuitry for a communication port for the system.
Figure 14:
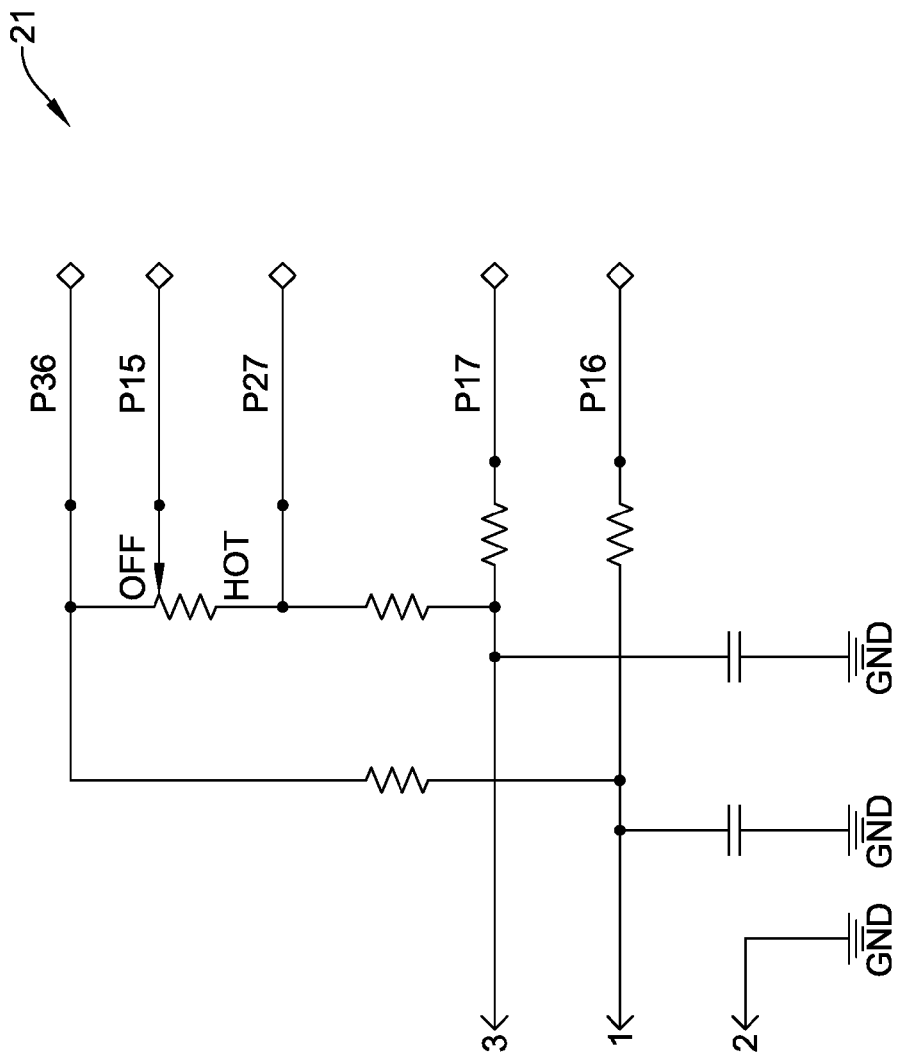
FIG. 14 is a diagram of circuitry for a temperature sensor and interface.
Figure 15:
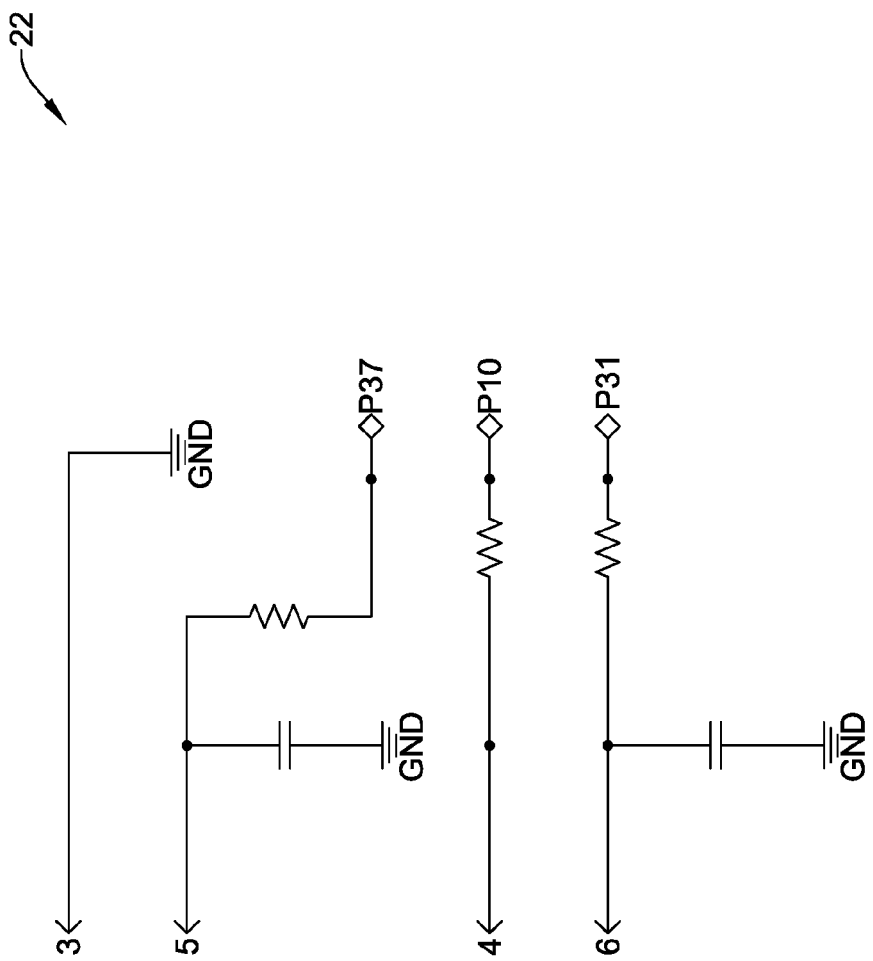
FIG. 15 is a diagram of circuitry for a flammable vapor sensor.
Figure 16:
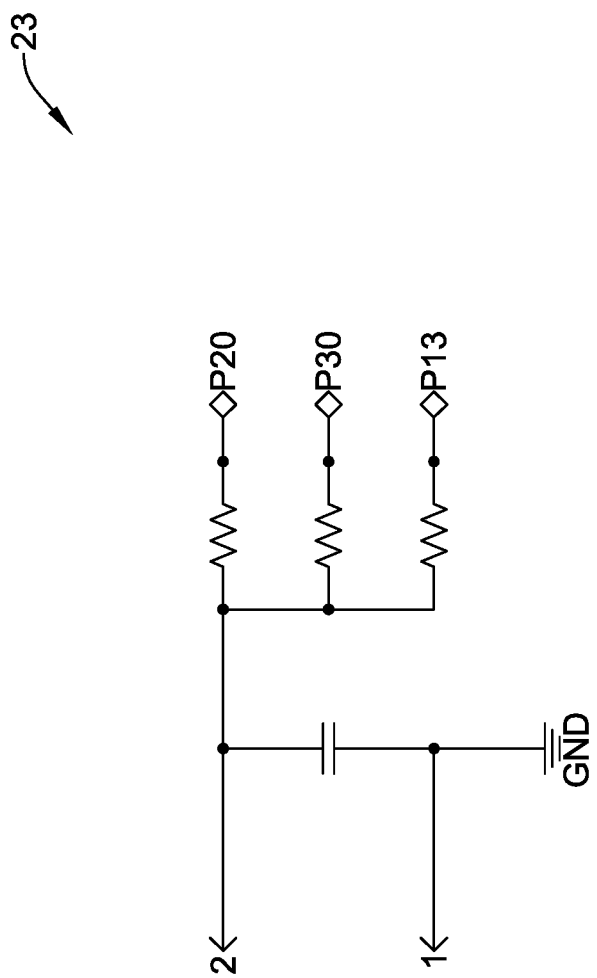
FIG. 16 is a diagram of circuitry for a door sensor.
Figure 17:
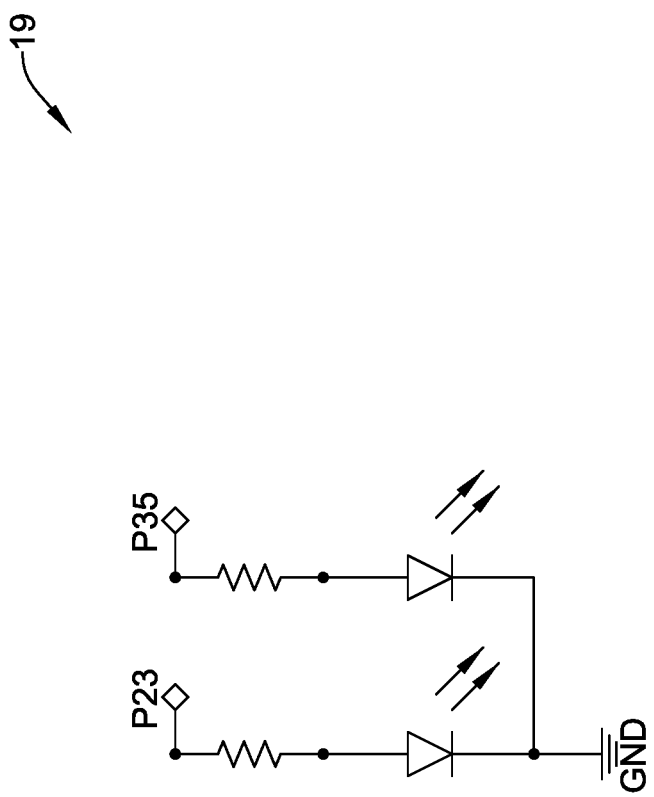
FIG. 17 is a diagram of circuitry for a light emitting diode indicator.

FIG. 13 is a diagram of circuitry for a communication port 18 for system 10. FIG. 14 is a diagram of circuitry for a temperature sensor and interface 21. FIG. 15 is a diagram of circuitry for a flammable vapor sensor 22. FIG. 16 is a diagram of circuitry for a door sensor 23. FIG. 17 is a diagram of circuitry for a two-color light emitting diode (LED) indicator 19.

To recap, a control circuit may incorporate a thermally activated power source, a valve pick circuit connected to the thermally activated power source, a safety switch circuit connected to the valve pick circuit, and a valve drive circuit connected to the safety switch circuit. The valve pick circuit may incorporate a charge storage device, a first switch for preventing current flow back to the thermally activated power source, and a second switch for allowing current to flow from the charge storage device to the safety switch circuit. The safety switch circuit may require not perfectly in phase input signals to turn on a third switch for allowing the current to flow from the second switch to the valve drive circuit.

The charge storage device may be charged to at least a first voltage before a valve pick time of the valve pick circuit. The first switch may be off during the valve pick time of the valve pick circuit. The third switch may be connected to the first and second switches and the charge storage device through the second switch. A fourth switch may be for receiving the not perfectly in-phase input signals to turn on the third switch.

The valve drive circuit may incorporate a fifth switch connected to the third switch, and a first terminal connected to the fifth switch, for a connection to a first valve. When the charge storage device is charged to at least the first voltage, the valve pick time begins and the second, third and fifth switches are turned on, current may flow from the charge storage device via the first connection to a first valve.

A magnitude of the current to the first valve may range from one to three times a minimum magnitude of current needed to operate the first valve.

The first, second, third, fourth and fifth switches may be transistors. The charge storage device may be a capacitor.

The first, third and fifth transistors may be N-channel field effect transistors (FETs). The second transistor may be an NPN bipolar transistor. The fourth transistor may be a PNP bipolar transistor.

The control circuit may further incorporate a microcontroller. The microcontroller may provide the not perfectly in phase input signals to the fourth switch to turn on the third switch.

The control circuit may further incorporate a single DC-to-DC converter connected to the thermally activated power source. The control circuit may further incorporate a voltage clamping circuit connected to an output of the single DC-to-DC converter and to an input of the microcontroller.

The thermally activated power source may incorporate a thermopile device. The thermopile device may incorporate two or more serially connected thermocouple devices. The microcontroller may be an ultra-low-power microcontroller.

An approach for controlling one or more valves, may incorporate applying thermal energy to a thermoelectric device, generating a first voltage potential from the thermal energy using the thermoelectric device, converting the first voltage potential to a second voltage potential using a power converter, operating a controller using the second voltage potential, storing a charge on a capacitor using a third voltage potential from the controller, permitting, via signals from the controller to a safety switch, the charge on the capacitor to flow as a current through the safety switch to a valve drive circuit, preventing the charge on the capacitor to flow to the thermoelectric device, and permitting the current to the valve drive circuit to have a magnitude that ranges from one to three times a minimum magnitude of current needed to operate a valve connected to the valve drive circuit.

The signals from the controller to the safety switch may not necessarily be perfectly in phase for permitting the charge on the capacitor to flow as a current through the safety to the valve drive circuit.

The approach for controlling one or more valves, may further incorporate operating an igniter for a heating element, and manually holding the valve, connected to the valve drive circuit, open for providing fuel to the heating element for obtaining a flame from the heating element.

The valve may be tension-loaded to close the valve. The flame may heat up the thermoelectric device to generate the first voltage potential. The valve may be held open until an occurrence of the minimum magnitude of current needed to operate the valve connected to the valve drive circuit. The heating element may be a pilot light.

A flame control system may incorporate a power source, a reverse current protection circuit connected to the power source, an energy storage circuit connected to the reverse current protection circuit, a safety switch connected to the energy storage circuit, and a drive circuit, for a fluid control mechanism, connected to the safety switch. Providing a certain electronic signal to the safety switch may permit current to flow from the energy storage circuit through the safety switch to the drive circuit for the fluid control mechanism.

The flame control system may further incorporate a microcontroller connected to the energy storage circuit and the safety switch. The microcontroller may provide the certain electronic signal to the safety switch for permitting current to flow from the energy storage circuit through the safety switch to the drive circuit for the fluid control mechanism.

The certain electronic signal may incorporate not perfectly in phase input signals.

The flame control system may further incorporate a microcontroller connected to the energy storage circuit, a single DC-to-DC converter connected to the power source, and a clamping circuit connected to the DC-to-DC converter and the microcontroller.

The power source may incorporate a thermoelectric generator. The fluid control mechanism may incorporate a fuel valve connected to a flame generator. The flame generator, upon receipt of fuel and ignition, may heat the thermoelectric generator to provide electrical power. The energy storage circuit may incorporate a capacitor.

A patent document that may be relevant is U.S. Pat. No. 6,959,876, issued Nov. 1, 2005, and entitled "Method and Apparatus for Safety Switch". U.S. Pat. No. 6,959,876, issued Nov. 1, 2005, is hereby incorporated by reference.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. A valve control circuit for controlling an electrically controlled gas valve of a water heater, the valve control circuit comprising:
   a thermally activated power source;
   a microcontroller powered by the thermally activated power source; and
   valve control circuitry operatively coupled to the microcontroller and the thermally activated power source, wherein the valve control circuitry is configured to open a switch that forms part of an electrical path that couples power from the thermally activated power source to the electrically controlled gas valve to close the electrically controlled gas valve when the valve control circuitry fails to receive a time varying control signal from the microcontroller that has one or more predetermined time varying signal characteristics.

2. The valve control circuit of claim 1, wherein the one or more predetermined time varying signal characteristics comprises a continuous time varying control signal.

3. The valve control circuit of claim 1, wherein the one or more predetermined time varying signal characteristics comprises a duty cycle.

4. The valve control circuit of claim 1, wherein the one or more predetermined time varying signal characteristics comprises a frequency.

5. The valve control circuit of claim 1, wherein the time varying control signal represents a differential between two time varying control signals provided by the microcontroller.

6. The valve control circuit of claim 5, wherein the one or more predetermined time varying signal characteristics comprises the two time varying control signals provided by the microcontroller having different frequencies and/or phases.

7. The valve control circuit of claim 1, wherein the switch comprises a transistor.

8. The valve control circuit of claim 1, wherein the valve control circuitry comprises a valve pick circuit that is configured to:
    store energy produced by the thermally activated power source; and
    release at least some of the stored energy to pick the electrically controlled gas valve upon reception of a pick signal from the microcontroller.

9. The valve control circuit of claim 8, wherein the valve pick circuit is configured to store energy on a capacitor, and to prevent the capacitor of the valve pick circuit from discharging into the thermally activated power source when picking the electrically controlled gas valve.

10. The valve control circuit of claim 9, wherein the valve control circuitry comprises a first transistor and a second transistor operatively coupled in series and between the thermally activated power source and the electrically controlled gas valve, wherein the first transistor includes an internal body diode with a cathode that is pointed toward the thermally activated power source and the second transistor includes an internal body diode with a cathode that is pointed toward the electrically controlled gas valve.

11. The valve control circuit of claim 10, wherein valve control circuitry is configured to turn the second transistor off when the valve pick circuit is picking the electrically controlled gas valve to prevent the capacitor of the valve pick circuit from discharging into the thermally activated power source.

12. The valve control circuit of claim 1, further including a switching circuit that is configured to reduce delivery of power produced by the thermally activated power source to the electrically controlled gas valve in order to close the electrically controlled gas valve or prevent the electrically controlled gas valve from opening when the switching circuit fails to receive a predetermined output from the microcontroller.

13. A valve control circuit for controlling an electrically controlled gas valve of a water heater, the valve control circuit comprising:
    a thermally activated power source;
    a microcontroller powered by the thermally activated power source;
    a valve pick circuit configured to:
        store energy produced by the thermally activated power source;
        release at least some of the stored energy to pick the electrically controlled gas valve upon reception of a pick signal from the microcontroller; and
        prevent the released stored energy from discharging into the thermally activated power source when picking the electrically controlled gas valve.

14. The valve control circuit of claim 13, wherein the valve pick circuit is configured to store energy on a capacitor.

15. The valve control circuit of claim 14, wherein the capacitor is charged using energy from a time varying signal provided by the microcontroller.

16. The valve control circuit of claim 14, wherein the valve control circuit is configured to prevent the capacitor of the valve pick circuit from discharging into the thermally activated power source when picking the electrically controlled gas valve.

17. The valve control circuit of claim 16, wherein the valve control circuit comprises a first transistor and a second transistor operatively coupled in series and between the thermally activated power source and the electrically controlled gas valve, wherein the first transistor includes an internal body diode with a cathode that is pointed toward the thermally activated power source and the second transistor includes an internal body diode with a cathode that is pointed toward the electrically controlled gas valve.

18. The valve control circuit of claim 17, wherein valve control circuit is configured to turn the second transistor off when the valve pick circuit is picking the electrically controlled gas valve to prevent the capacitor of the valve pick circuit from discharging into the thermally activated power source.

19. The valve control circuit of claim 13, further comprising a switching circuit that is configured to reduce delivery of power produced by the thermally activated power source to the electrically controlled gas valve in order to close the electrically controlled gas valve or prevent the electrically controlled gas valve from opening when the switching circuit fails to receive a predetermined output from the microcontroller.

20. A water heater comprising:
    a water tank for holding heated water;
    a burner for heating water in the water tank;
    an electrically controlled gas valve for providing gas to the burner;
    a water heater controller operatively coupled to the electrically controlled gas valve, the water heater controller comprising a valve control circuit for controlling the electrically controlled gas valve, the valve control circuit comprising:
        a thermally activated power source;
        a microcontroller powered by the thermally activated power source;
        a valve pick circuit configured to:
            store energy produced by the thermally activated power source;
            release at least some of the stored energy to pick the electrically controlled gas valve upon reception of a pick signal from the microcontroller; and
            prevent the released stored energy from discharging into the thermally activated power source when picking the electrically controlled gas valve.

21. The water heater of claim 20, wherein the valve pick circuit is configured to store energy on a capacitor.

22. The water heater of claim 21, wherein the capacitor is charged using energy from a time varying signal provided by the microcontroller.

23. The water heater of claim 21, wherein the valve control circuit is configured to prevent the capacitor of the valve pick circuit from discharging into the thermally activated power source when picking the electrically controlled gas valve.

24. The water heater of claim 23, wherein the valve control circuit comprises a first transistor and a second transistor operatively coupled in series and between the thermally activated power source and the electrically controlled gas valve, wherein the first transistor includes an internal body diode with a cathode that is pointed toward the thermally activated power source and the second transistor includes an internal body diode with a cathode that is pointed toward the electrically controlled gas valve.

25. The water heater of claim 24, wherein the valve control circuit is configured to turn the second transistor off when the valve pick circuit is picking the electrically controlled gas valve to prevent the capacitor of the valve pick circuit from discharging into the thermally activated power source.

26. The water heater of claim 20, wherein the valve control circuit further comprises a switching circuit that is configured to reduce delivery of power produced by the thermally activated power source to the electrically controlled gas valve in order to close the electrically controlled gas valve or prevent the electrically controlled gas valve from opening when the valve control circuit fails to receive a predetermined output from the microcontroller.

27. A water heater comprising:
a water tank for holding heated water;
a burner for heating water in the water tank;
an electrically controlled gas valve for providing gas to the burner;
a water heater controller operatively coupled to the electrically controlled gas valve, the water heater controller comprising a valve control circuit for controlling the electrically controlled gas valve, the valve control circuit comprising:
a thermoelectric power source;
a microcontroller powered by the thermoelectric power source;
a pick capacitor for storing energy produced by the thermoelectric power source;
circuitry configured to release at least some of the energy stored on the pick capacitor to the electrically controlled gas valve to pick the electrically controlled gas valve upon reception of a pick signal from the microcontroller;
the circuitry further configured to prevent the energy released from the pick capacitor from discharging into the thermoelectric power source when picking the electrically controlled gas valve; and
the circuitry further configured to open a switch that forms part of an electrical path that couples power from the thermoelectric power source to the electrically controlled gas valve to close the electrically controlled gas valve when the circuitry fails to receive a time varying control signal from the microcontroller that has one or more predetermined time varying signal characteristics.

28. The water heater of claim 27, wherein the circuitry that is configured to prevent the energy released from the pick capacitor from discharging into the thermoelectric power source when picking the electrically controlled gas valve comprises a transistor forming part of an electrical path between the pick capacitor and the thermoelectric power source, wherein the transistor includes an internal body diode with a cathode that is pointed toward the pick capacitor.

29. The water heater of claim 27, wherein the switch comprises a transistor.

30. The water heater of claim 27, wherein the circuitry further comprises a switching circuit that is configured to reduce delivery of power produced by the thermoelectric power source to the electrically controlled gas valve in order to close the electrically controlled gas valve or prevent the electrically controlled gas valve from opening when the circuitry fails to receive a predetermined output from the microcontroller.

* * * * *